United States Patent [19]

Speicher et al.

[11] Patent Number: 4,603,705
[45] Date of Patent: Aug. 5, 1986

[54] INTRAVASCULAR MULTIPLE ELECTRODE UNITARY CATHETER

[75] Inventors: Vernon L. Speicher, Leechburg; Stanley M. Bach, Jr., Pittsburgh, both of Pa.

[73] Assignee: Mieczyslaw Mirowski, Owings Mills, Md.

[21] Appl. No.: 606,948

[22] Filed: May 4, 1984

[51] Int. Cl.$^4$ .............................................. A61N 1/05
[52] U.S. Cl. .............................. 128/786; 128/419 D
[58] Field of Search ............... 128/419 D, 419 P, 642, 128/784-786

[56] References Cited

U.S. PATENT DOCUMENTS

| | | | |
|---|---|---|---|
| 3,804,098 | 4/1974 | Friedman | 128/786 |
| 3,857,398 | 12/1974 | Rubin | 128/419 D |
| 3,942,536 | 3/1976 | Mirowski et al. | 128/419 D |
| 4,030,509 | 6/1977 | Heilman et al. | 128/419 D |
| 4,161,952 | 7/1979 | Kinney et al. | 128/786 |
| 4,184,493 | 1/1980 | Langer et al. | 128/419 D |
| 4,202,340 | 9/1981 | Langer et al. | 128/419 D |
| 4,262,673 | 4/1981 | Kinney et al. | 128/419 P |
| 4,291,699 | 9/1981 | Geddes et al. | 128/419 D |
| 4,355,646 | 10/1982 | Kallok et al. | 128/786 |
| 4,481,953 | 11/1984 | Gold et al. | 128/786 |
| 4,499,907 | 2/1985 | Kallok et al. | 128/786 |

FOREIGN PATENT DOCUMENTS 1182866  2/1985  Canada .

OTHER PUBLICATIONS

"Role of a Catheter Lead System for Transvenous Countershock and Pacing During Electrophysiologic Tests: An Assessment of the Usefulness of Catheter Shocks for Terminating Ventricular Tachyarrhythmias," by Lawrence E. Waspe et al., The American Journal of Cardiology, Sep. 1, 1983, vol. 52, pp. 477-484.

Primary Examiner—Lee S. Cohen
Attorney, Agent, or Firm—Fleit, Jacobson, Cohn & Price

[57] ABSTRACT

A multiple electrode unitary intravascular cardiac catheter comprising a distal electrode for sensing and pacing, an intermediate electrode for sensing, pacing and cardioverting, and a proximal electrode for sensing and cardioverting. The catheter may also be employed in combination with an external patch electrode.

10 Claims, 12 Drawing Figures

INTRAVASCULAR MULTIPLE ELECTRODE UNITARY CATHETER

BACKGROUND OF THE INVENTION

1. Field of the Invention

The present invention is directed to a multiple electrode unitary intravascular catheter designed for use in a system which continually monitors heart function and, upon detection of abnormal function, provides either pacing energy or cardioverting energy as required. The unitary intravascular catheter is in one or more ways more versatile, more compact or more easily implanted than previous multiple electrode systems capable of functioning in the same modes. Additionally, the unitary catheter, which comprises a distal electrode, an intermediate electrode, and a proximal electrode, provides superior sensing capability immediately following cardioversion as compared to the prior art two-electrode catheters. Where a modified cardioverting energy distribution is required, the single intravascular catheter may be used in conjunction with other electrodes, such as a patch electrode applied to the external surface of the heart.

2. Description of the Prior Art

During the past several decades, coronary heart disease has become the primary cause of death in the developed areas of the world. Close to 1.5 million Americans will suffer a heart attack this year, with nearly 350,000 of them dying suddenly following the myocardial infarction. Although the precise cause of sudden death in coronary heart disease has not yet been entirely clarified, the available evidence permits the medical field to ascribe death in the majority of sudden death cases to rapid disturbances in cardiac electrical activity known as tachyarrhythmia. Tachyarrhythmic heart conditions which may be lethal, are ventricular tachycardia, ventricular flutter, and ventricular fibrillation. Atrial tachyarrhythmic conditions such as atrial tachycardia and fibrillation only become life threatening when they lead to rapid ventricular disturbance.

Excessively slow rhythm disturbances, known as bradyarrhythmias, are involved in a minority of cases. Bradyarrhythmic conditions become serious when there is a defect in impulse formation or in the normal cardiac conduction system without adequate "escape" rhythm.

Within the hospital environment, recent experience has demonstrated that tachyarrhythmic conditions are often reversible phenomena and may be corrected by applying relatively high energy electrical shocks to the heart. Bradyarrhythmic conditions, although not as often fatal, are often correctable by pacemaking pulses of very low energy. The correction of arrhythmic heart conditions by application of relatively high energy electrical shock to the heart will, for the purposes of this invention, be referred to as "cardioversion".

In recent years, substantial progress has been made in the development of techniques for effectively terminating various tachyarrhythmias. Recent developments include implantable electronic standby defibrillators which, in response to the detection of an abnormally rapid cardiac rhythm, discharge sufficient energy via electrodes connected to the heart to depolarize and restore the heart to normal cardiac rhythm.

Considerable sophistication now exists with regard to techniques for reliably monitoring heart activity in order to determine whether cardioversion is necessary. Included among such techniques are those which monitor ventricular rate to determine the presence of fibrillation on the basis of a probability density function (PDF), a technique described in commonly owned U.S. Pat. Nos. 4,184,493 and 4,202,340, both of Langer et al, and a more recent system which is disclosed in commonly owned co-pending application Ser. No. 175,670 of Langer et al, filed Aug. 5, 1980, now abandoned, utilizing both the PDF technique to determine the presence of an abnormal cardiac rhythm and a heart rate sensing circuit for distinguishing between ventricular fibrillation and high-rate tachycardia, on the one hand, and a normal sinus rhythm or low-rate tachycardia, on the other hand.

Commonly owned, co-pending application Ser. No. 478,038 of Imran et al, filed Mar. 23, 1983, discloses a cardioversion system including an implantable defibrillator and an external non-invasive controller/monitor for altering the state and/or retrieving status information from the implanted defibrillator. The implantable defibrillator comprises a high-voltage inverter circuit with shunt-prevention means; a combination of a PDF circuit and a heart-rate analysis circuit, each circuit detecting abnormal cardiac rhythms and both circuits jointly activating the high-voltage inverter circuit; a plurality of electrodes connected to the heart, including bipolar sensing electrodes, coupled with the heart-rate analysis circuit, for sensing ventricular activity; high-voltage pulse delivery electrodes, coupled with the high-voltage inverter circuit; circuits for, respectively, delivering high-energy, defibrillating pulses, and providing PDF information signals; a pulse counter/memory for counting and storing the number of defibrillating pulses issued by the inverter circuit; a piezoelectric speaker, coupled to the wall of a case enclosing the defibrillator circuits, for generating audible tones indicative of the status of the defibrillator; and means responsive to an external magnet for changing the state of the defibrillator.

Technology now exists for the development of implantable devices capable of both pacing and cardioverting, each in response to a sensing mechanism which is incorporated in the implantable device. The electrodes for sensing cardiac electrical abnormalities, as well as for delivering electrical impulses to the heart, are an extremely important consideration in the entire pacing/cardioverting system. U.S. Pat. No. 3,942,536 to Mirowski et al discloses a single intravascular catheter electrode system which monitors heart function and provides the malfunctioning heart with electrical shocks of sufficient amplitude to restore the heart to normal sinus rhythm.

U.S. Pat. No. 4,030,509, issued to Heilman et al, discloses several embodiments of an electrode system for use in ventricular defibrillation wherein the electrodes are applied to the exterior surface of the heart.

U.S. Pat. No. 4,161,952, issued to Kinney et al, discloses a catheter electrode including a resilient, wound wire discharge electrode having proximal and distal ends. The proximal end of the lead is adapted for connection to a pulse generator. The lead is connected to the wound wire discharge electrode both at the proximal and distal ends thereof, and the catheter electrode system is designed for positioning in the superior vena cava or in the coronary sinus, and preferably acts against an independent apex electrode. Thus, the electrode system of Kinney et al is not of unitary design.

U.S. Pat. No. 4,355,646, issued to Kallok et al, discloses a lead having multiple electrodes which is intravenously implanted for use in patients having a high risk of ventricular fibrillation. The lead comprises four electrodes, the two distal electrodes being spaced for optimal measurement of impedance changes due to mechanical contractions and used for mechanical sensing of normal cardiac activity. The two proximal electrodes are spaced from the distal electrodes so as to ensure their placement within the superior vena cava; the two distal electrodes serve to deliver the defibrillation energy.

None of the prior art references noted above discloses an effective multiple electrode unitary intravascular catheter capable of sensing heart abnormality and delivering either defibrillating energy or pacing energy in response to the abnormality for restoring normal heart function.

Additionally, none of the prior art devices noted above is capable of delivering a high-energy discharge through a single catheter and immediately being able to effectively sense the heart's electrical activity through the same catheter. Following cardioversion, the tissue in the area immediately adjacent the discharge electrodes at least temporarily loses a substantial portion of its ability to conduct electrical impulses due to the high electrical energy just applied to the area. Full recovery most often results, but there is a time when electrical conduction suffers. This phenomenon deleteriously impacts on the sensing capability of the prior art devices which sense and cardiovert from the same two electrodes, at least at a time when sensing is of utmost importance.

Further, the prior art electrodes were somewhat limited in their capability for integration with other electrodes in the event that pacing, cardioverting, or sensing could more effectively be accomplished through alternate electrode configurations.

Thus, a need has continued to exist for a unitary multiple electrode catheter capable of sensing, pacing and cardioverting the heart, with an improved sensing capability immediately following cardioversion, and having the flexibility to permit integration with other electrodes in the event that a more effective distribution of the electrical energy is attainable.

SUMMARY OF THE INVENTION

It is an object of this invention to provide a multiple electrode unitary catheter.

It is another object of this invention to provide a multiple electrode unitary catheter which can be intravascularly positioned.

It is still an object of this invention to provide a multiple electrode unitary catheter capable of sensing, pacing, and cardioverting heart abnormalities.

It is a further object of the instant invention to provide a multiple electrode unitary catheter capable of accurately sensing heart activity immediately following cardioversion.

It is yet an object of the instant invention to provide a multiple electrode unitary catheter capable of integration with a patch electrode by replacement of one of the cardioverting electrodes with the patch electrode where better energy distribution is required.

These and other objects as will hereinafter become more apparent are accomplished by a unitary multiple electrode catheter comprising a distal electrode, an intermediate electrode and a proximal electrode, heart rate sensing and pacing being provided by the distal electrode in combination with the intermediate electrode and PDF sensing and cardioversion being provided by the intermediate electrode in combination with the proximal electrode.

The instant catheter provides continued, accurate sensing of heart rate activity following cardioversion because it utilizes different electrodes and an advanced electrode placement; therefore, different heart tissue is involved in the rate sensing activity on the one hand and the cardioverting activity on the other hand.

Further, because the instant catheter is compact and yet very versatile, it can be combined with other electrodes simply by changing a connection at the pulse generator.

These and other advantages of the invention will become more readily apparent when reference is made to the following description taken in conjunction with the accompanying drawings.

BRIEF DESCRIPTION OF THE DRAWINGS

FIG. 1a is an enlarged fragmentary cross section of that portion of FIG. 1 between the distal tip and the line 1a—1a.

FIG. 1e is an enlarged fragmentary cross-sectional view of that portion of FIG. 1 showing elements 80, 86 and 86a.

DESCRIPTION OF THE PREFERRED EMBODIMENT

Figure 1:
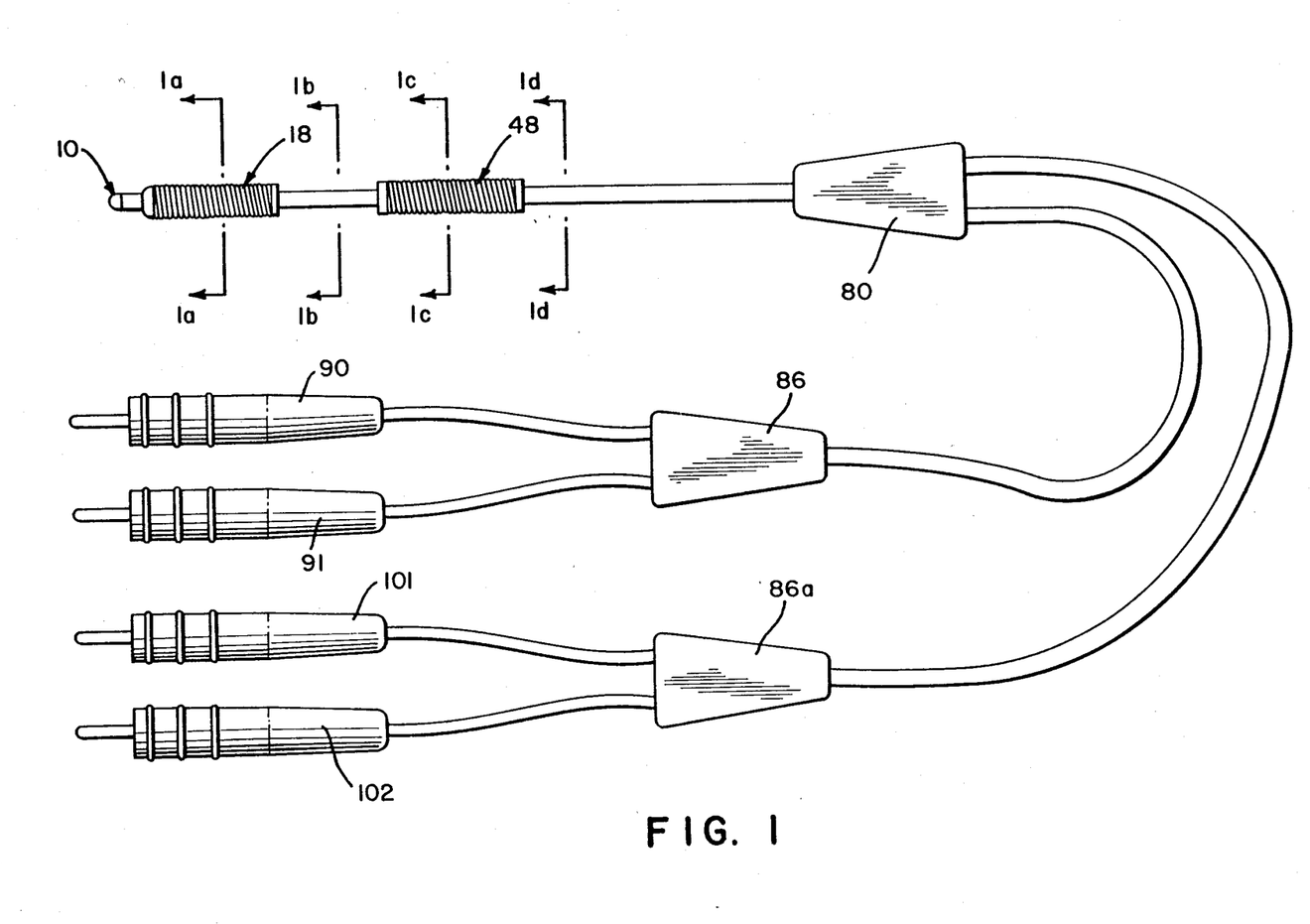
FIG. 1 is a side view of the multiple electrode unitary intravascular pacing, cardioverting, and sensing catheter of the present invention.
Figure 1A:
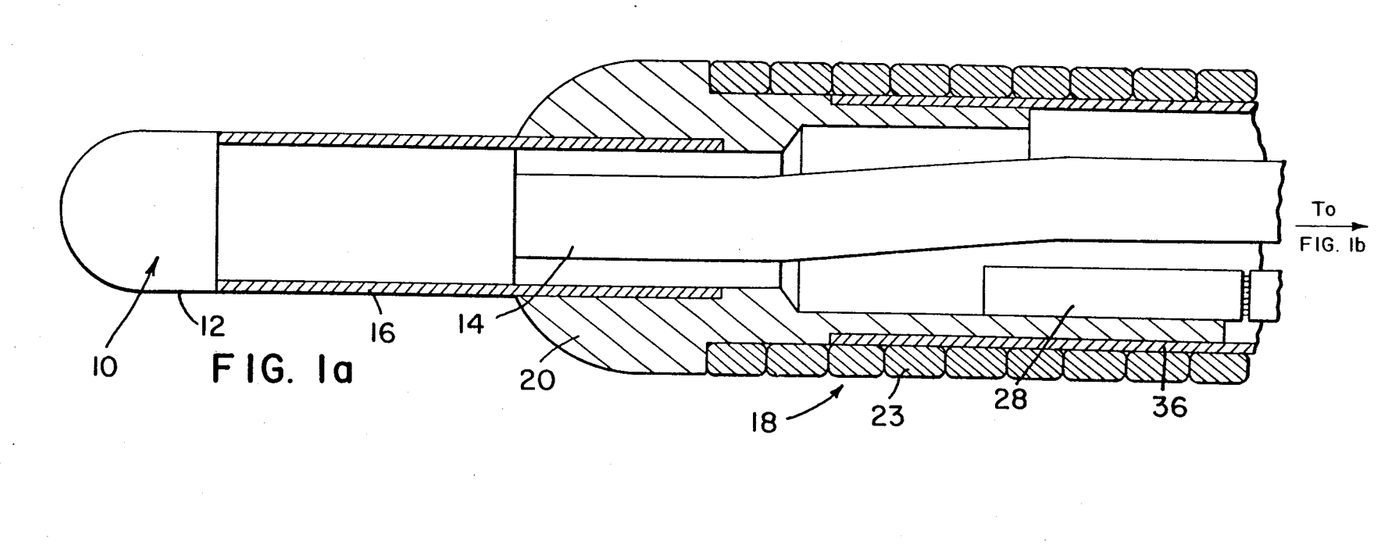

The following description refers to FIGS. 1 and 1a through 1i of the drawings, hereinafter referred to collectively as "FIG. 1", where there is illustrated a plan view of a multiple electrode unitary catheter for sensing, cardioverting, and pacing comprising a distal electrode 10, an intermediate electrode 18, and a proximal electrode 48. Distal electrode 10 comprises a distal tip 12 and lead 14, said lead 14 providing electrical conductivity between distal tip 12, via element 91 (FIG. 1h), through heart lead coil 98, and terminating at male plug 96. Distal tip 12 has a diameter in the range of 2.0–2.8 mm, a length in the range of 0.5–2.0 mm, and a surface area on the order of about 10–20 mm$^2$. Typically, the distal tip is constructed of a platinum, iridium alloy containing approximately 10% iridium. Distal electrode 10, in conjunction with intermediate electrode 18, provides sensing and pacing functions.

The electrical conductor 98 (FIG. 1h) of lead 14 (FIG. 1a) is encased by an insulating tubing such as of Silastic, said insulating tubing typically having an outside diameter of 1.07 mm and an inside diameter of 0.81 mm. Lead coil 98 terminates in male plug 96, adapted for insertion into an implantable device, not shown.

Distal electrode 10 is separated from intermediate electrode 18 by tubing 16. Tubing 16 acts to hold the distal tip in place, to seal the internal catheter from the body fluids, to provide proper spacing between distal electrode 10 and intermediate electrode 18, and to electrically insulate distal electrode 10 from intermediate electrode 18. Typically, tubing 16 takes the form of a suitable insulating tubing such as Silastic having a wall thickness defined by an outside diameter in the range of 1.8–2.8 mm and an inside diameter in the range of 1.8–2.0 mm. One critical aspect in the electrode of this invention lies in the spacing between distal electrode 10 and intermediate electrode 18. It is preferred that the spacing between these two electrodes lies in the range of 1 to 10 mm. An optimal distance between the two electrodes is 4 mm.

Figure 1B:
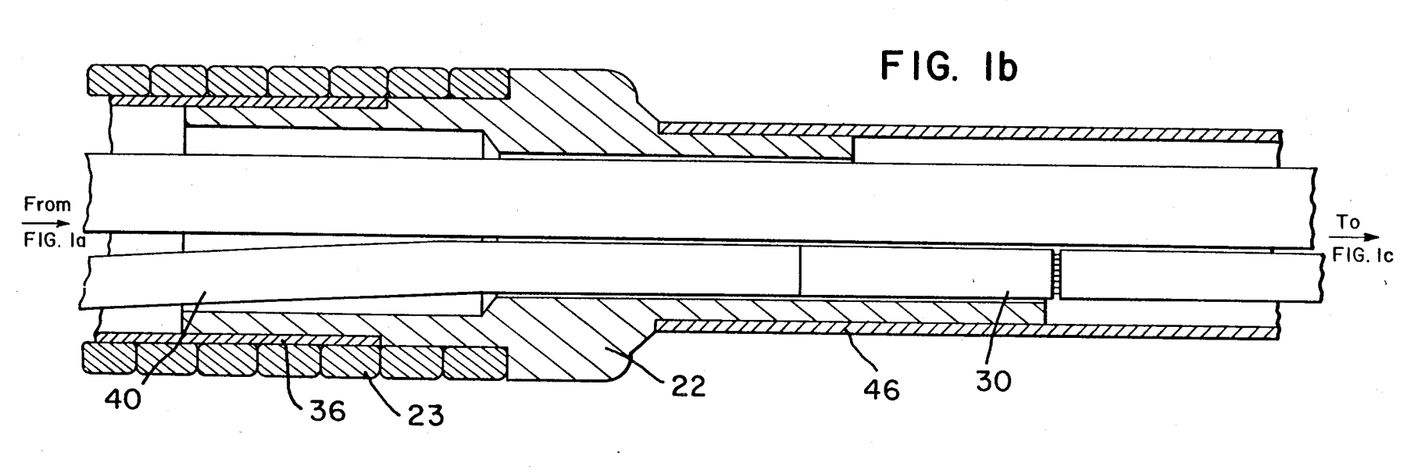
FIG. 1b is an enlarged fragmentary cross-sectional view of that portion of FIG. 1 between lines 1a—1a and 1b—1b.
Figure 1C:
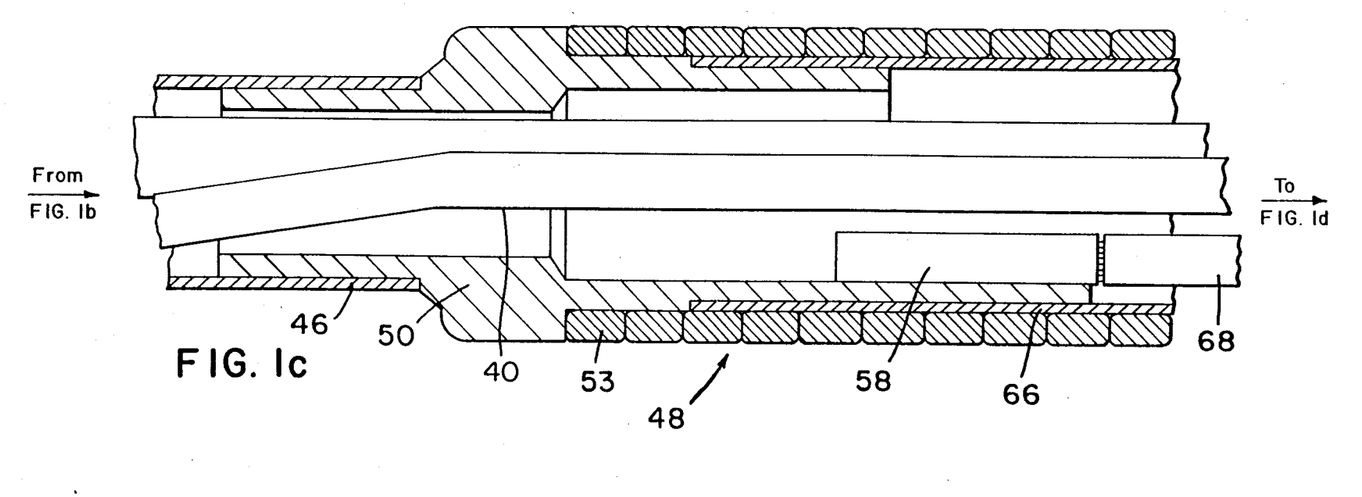
FIG. 1c is an enlarged fragmentary cross-sectional view of that portion of FIG. 1 between lines 1b—1b and 1c—1c.
Figure 1D:
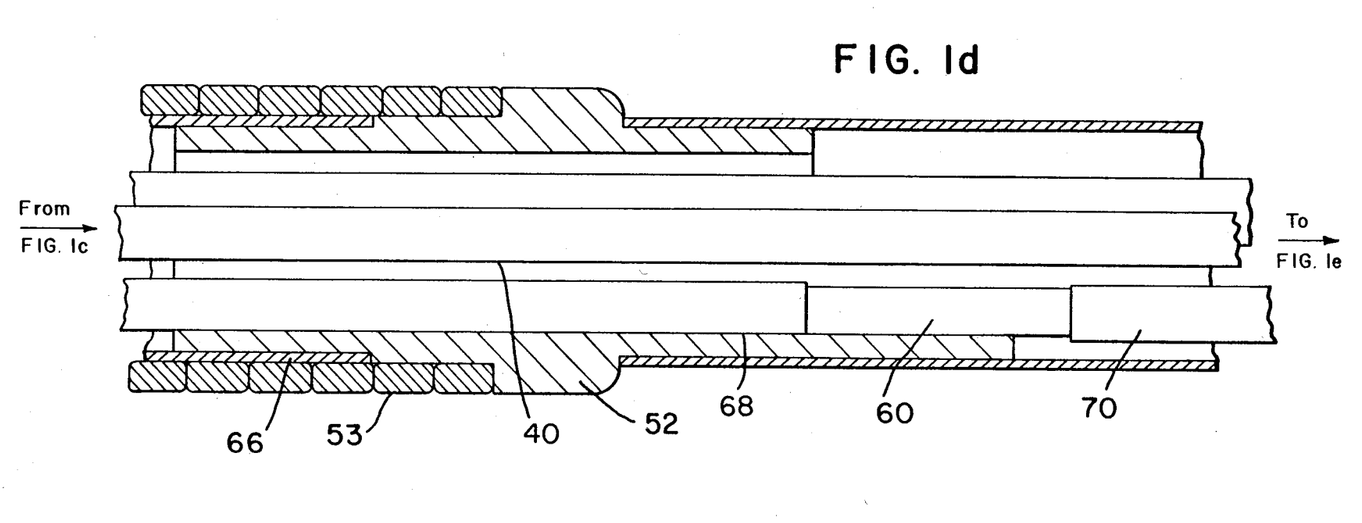
FIG. 1d is an enlarged fragmentary view of that portion of FIG. 1 between lines 1c—1c and 1d—1d.
Figure 1E:
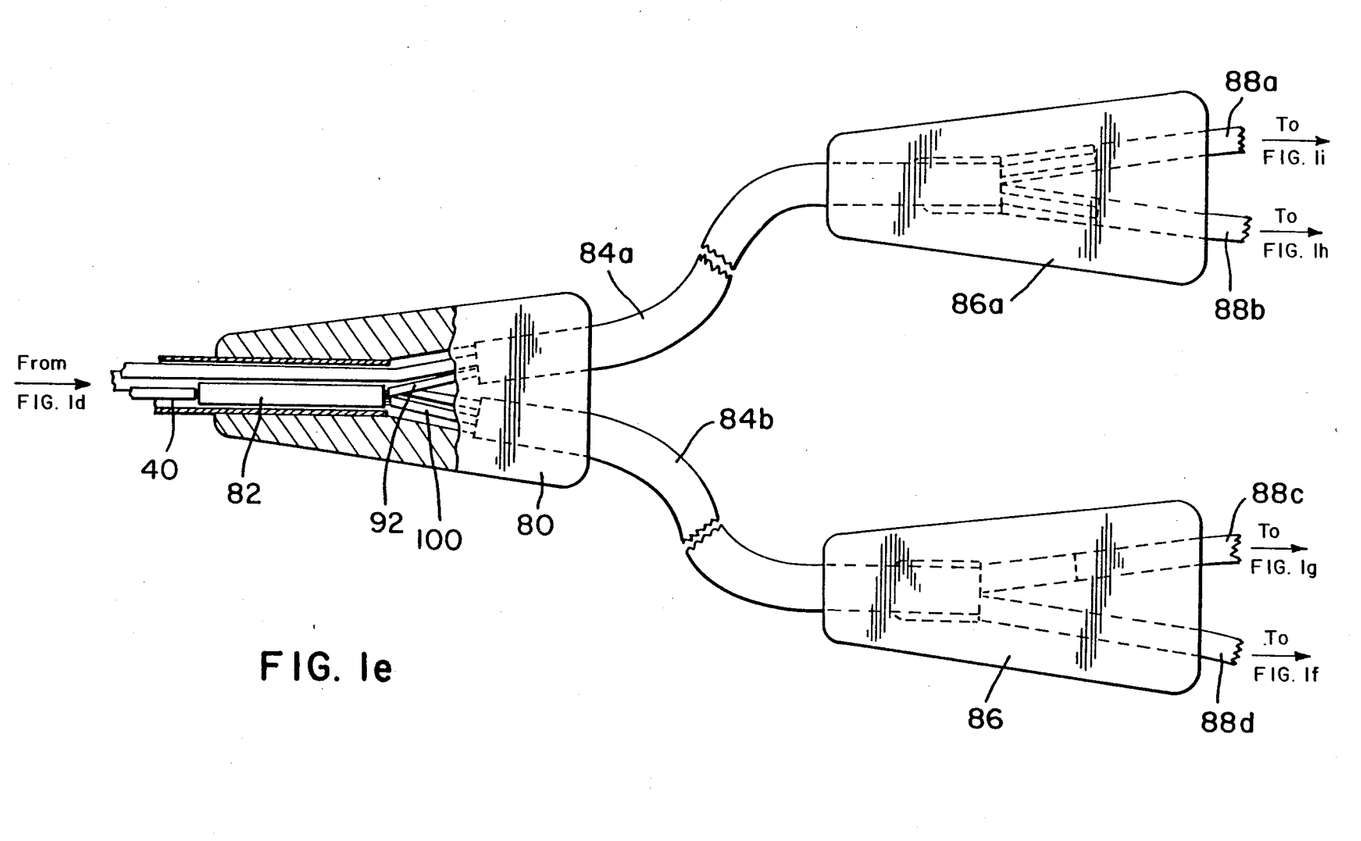
Figure 1F:
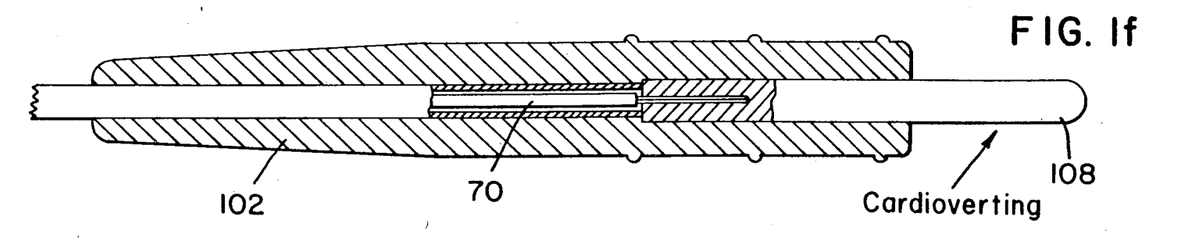
FIG. 1f is an enlarged fragmentary cross-sectional view of that portion of FIG. 1 showing element 102.
Figure 1G:
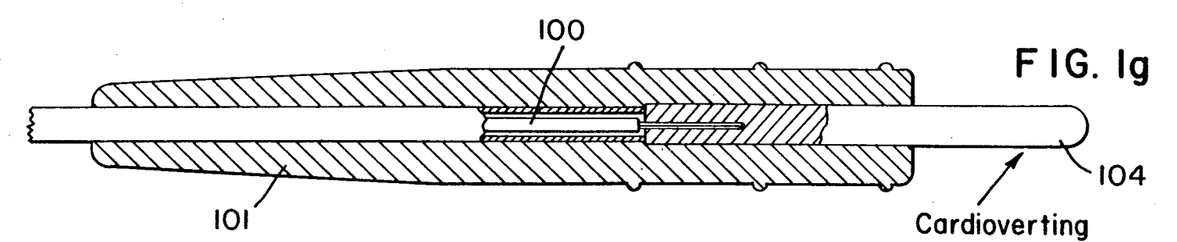
FIG. 1g is an enlarged fragmentary cross-sectional view of that portion of FIG. 1 showing element 101.
Figure 1H:
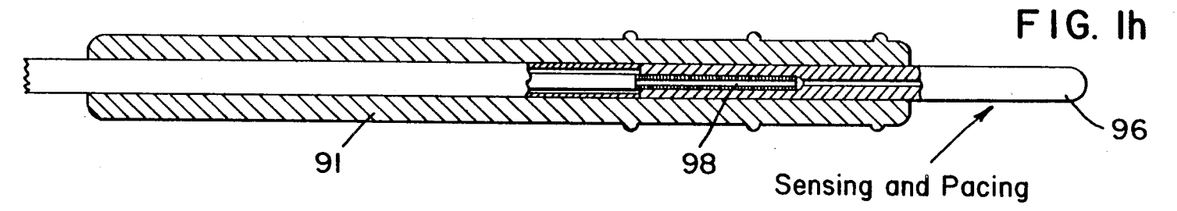
FIG. 1h is an enlarged fragmentary cross-sectional view of that portion of FIG. 1 showing element 91.
Figure 1I:
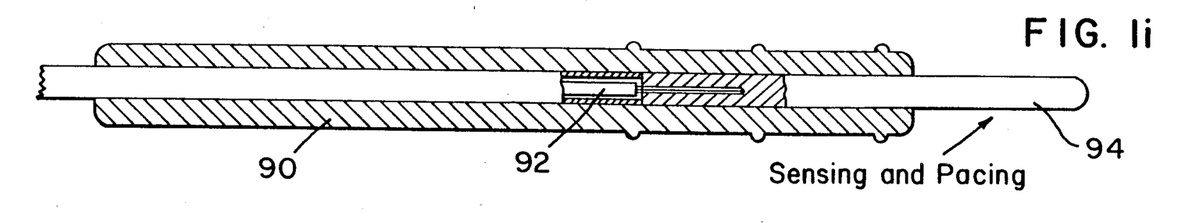
FIG. 1i is an enlarged fragmentary cross-sectional view of that portion of FIG. 1 showing element 90.

Intermediate electrode 18 comprises lead fittings 20 and 22, spring 23, said spring 23 comprising an electrically conductive wound wire surface, two electrically conductive tubings 28 and 30, said two electrically conductive tubings 28 and 30 connected in parallel, DBS wires 40, 92 and 100, and male plugs 94 and 104 (see FIGS. 1i and 1g). Lead fittings 20 and 22 and spring wire 23 comprise an electrically conductive material inert to body fluids. C. P. titanium or platinum coated C. P. titanium is a preferred material for this utility. Lead fitting 20 provides electrical contact between electrically conductive surface 23 and electrically conductive tubing 28; lead fitting 22 provides electrical contact between electrically conductive surface 23 and electrically conductive tubing 30. Spring 23 has a length in the range of about 20 to 50 mm and a diameter in the range of about 3.0 to 4.0 mm. This spring is close-wound, and is preferably wound to approximately 20 turns per inch. The close-wound spring provides a continuous electrically conductive surface which maintains its flexibility while still lowering the impedance of the electrode and thus permitting more current to be delivered. Typically, the surface area for intermediate electrode 18 is in the range of about 30 to 50 mm$^2$, with about 43 mm$^2$ being the preferred surface area. Another important aspect of the present invention involves the length of the intermediate electrode 18 as measured from the outside edges of lead fittings 20 and 22. It is preferred that this length be in the range of about 20 to 50 mm, with about 38 mm being optimal. Insulative tubing 36 typically comprises a Silastic material, having an outside diameter of about 2.8 mm and an inside diameter of about 2.4 mm. Tubing 36 provides insulative separation between conductive lead fittings 20 and 22 and, additionally, seals the internal catheter from body fluids. Electrically conductive tubings 28 and 30 are made of an electrically conductive material, typically stainless steel, and provide electrical contact between DBS wire 40 and lead fittings 20 and 22. DBS wire 40 is drawn, brazed, stranded wire, typically a mixture of stainless steel and silver, and provides means for electrical transmission for intermediate electrode 18. Thus, intermediate electrode 18, acting through spring element 23, provides sensing, pacing, and cardioverting capability, coacting with distal electrode 10 to provide sensing and pacing and coacting with proximal electrode 48 to provide sensing and cardioversion.

Tubing 46 is typically an insulating tubing, such as Silastic, typically having an outside diameter of 3.2 mm and an inside diameter of 2.0 mm and serves to electrically insulate intermediate electrode 18 from proximal electrode 48, seal the internals of the catheter from body fluids, provide sufficient flexibility in the catheter to provide for proper insertion and prevent perforation of the heart. Additionally, tubing 46 provides for proper spacing between intermediate electrode 18 and proximal electrode 48. It is preferred that this distance be in the range of about 8 to 14 centimeters, with about 11 centimeters being optimal.

Proximal electrode 48 (FIG. 1c) comprises lead fittings 50 and 52, spring 53, said spring 53 comprising an electrically conductive wound wire surface, electrically conductive tubings 58 and 60, tubing 66, DBS wire 68, DBS wire 70, and male plug 108 (FIG. 1f). Lead fittings 50 and 52, and spring 53 comprise electrically conductive materials which are inert to body fluids. Typically, these elements are made of C. P. titanium, platinum, iridium, or platinum coated titanium. Electrically conductive tubings 58 and 60 are typically stainless steel and are connected in parallel by DBS wire 68. It is contemplated that proximal electrode 48, as measured from the outside edges of lead fittings 50 and 52, be in the range of about 5 to 10 cm, with approximately 7.5 cm being optimal, and have a diameter in the range of about 3.0 to 4.0 mm. Proximal electrode 48, acting through spring 53 and male plug 108, and paired with intermediate electrode 18, provides cardioverting means as well as PDF sensing means. DBS wires 68 and 70 are drawn, brazed, stranded wire, typically a mixture of stainless steel and silver, and provide electrical connection between male plug 108, adapted for insertion into an implantable electrical device for sensing pacing and cardioverting, and spring 53.

Elements 80, 86 and 86a are reinforcing members. Element 82 is a splice and provides for integration of DBS wire 92 and DBS wire 100. After integration, these two wires become DBS wire 40 (FIG. 1b). Elements 84a and 84b are typically insulating tubing such as Silastic, typically having an outer diameter of about 3 mm and an inner diameter of about 2 mm. Elements 88a, 88b, 88c and 88d are typically insulating tubing such as Silastic, typically having an outer diameter of about 1.95 mm and an inner diameter of about 1.25 mm. Each of these tubing elements electrically insulates its respective lead and protects it from body fluids. Elements 90, 91, 101 and 102 are proximal boots and provide for adaptive insertion and sealing, respectively, of the male plugs 94, 96, 104 and 108 into the implantable electrical device. Similar devices are described in U.S. Pat. No. 4,262,673. One of the male plugs 94, 96, 104, and 108, in a manner known to the prior art, is hollow and thus adapted for insertion of a stylette, the stylette facilitating directional control of the catheter during its placement in the heart.

The three-electrode catheter of the present invention represents a substantial advance over prior art catheters. Because heart rate sensing and pacing are accomplished by the distal electrode in conjunction with the intermediate electrode, while higher energy cardioversion is accomplished by the intermediate electrode in conjunction with the proximal electrode, the instant catheter maintains its capability for heart rate sensing and low threshold pacing following cardioversion. Because the at least temporary depolonization of heart tissue due to higher voltage cardioversion affects heart tissue different from that involved with the rate sensing and pacing functions, the catheter continues to perform its rate sensing and low threshold pacing on undamaged heart tissue.

Figure 2:
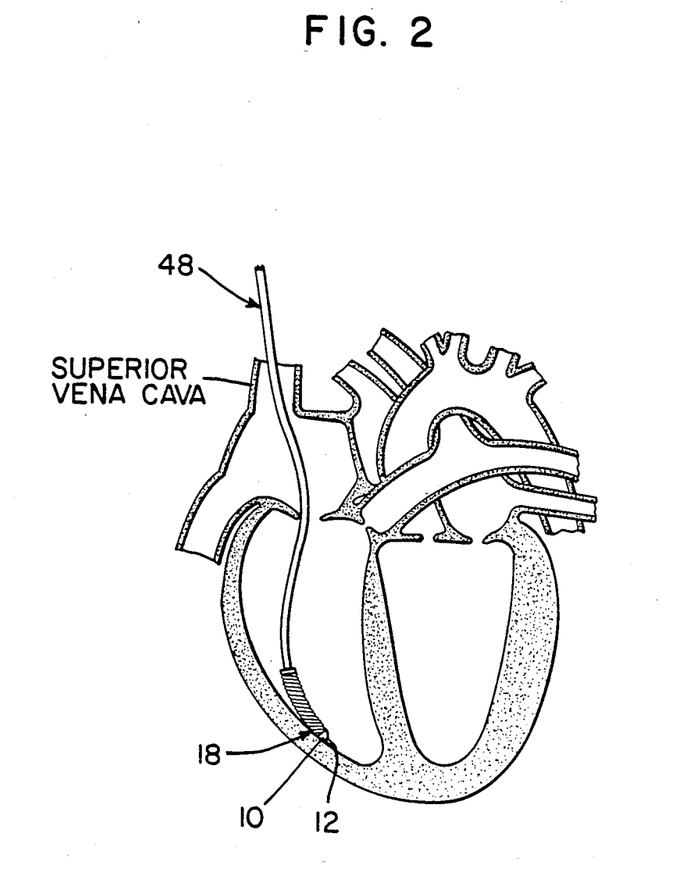
FIG. 2 is a cross-sectional view depicting the catheter of the present invention positioned in the heart.

Referring now to FIG. 2, there is depicted one possible position of the catheter electrode system of the present invention in a heart for effecting ventricular defibrillation. Distal electrode 10, comprising distal tip 12, and intermediate electrode 18 is wedged in the apex of the right ventricle. Proximal electrode 48 is in the right atrium and superior vena cava, straddling their junction.

Figure 3:
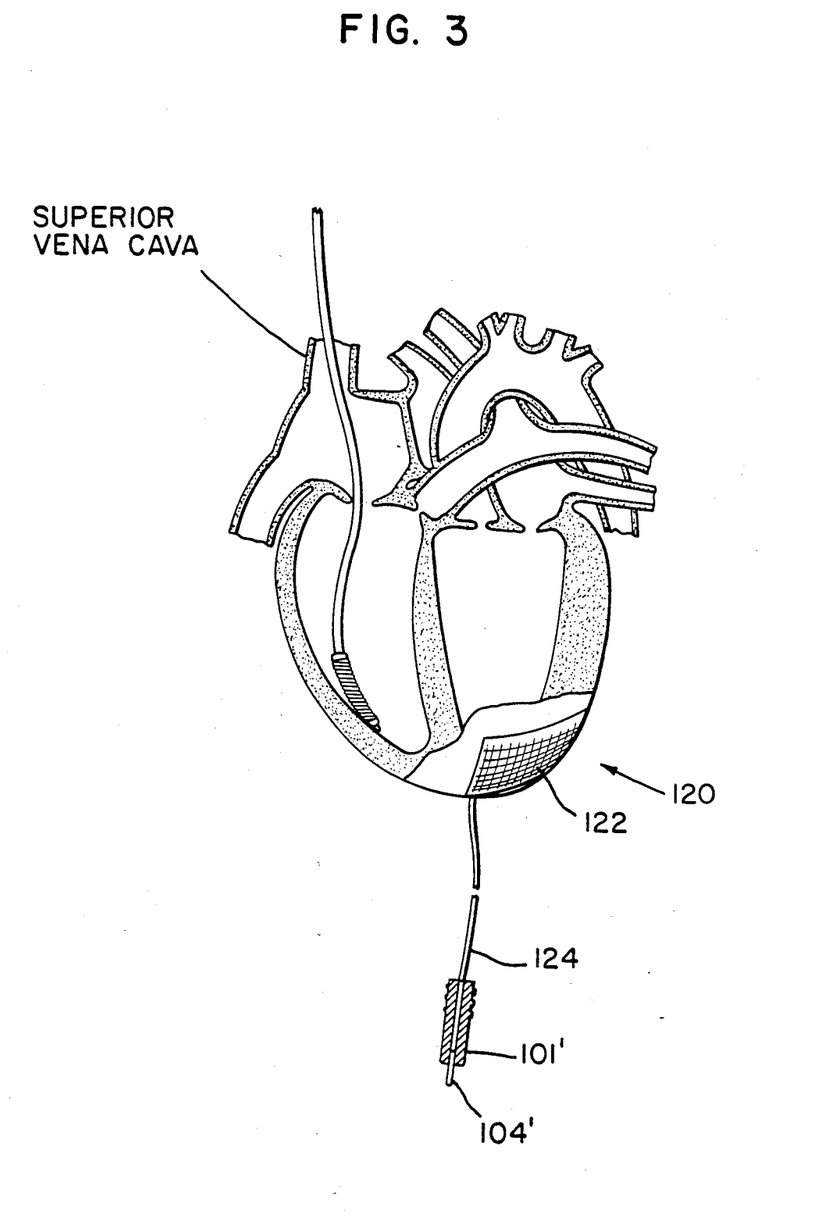
FIG. 3 is a cross-sectional view of an embodiment wherein the unitary intravascular catheter is used in conjunction with an external patch electrode.

FIG. 3 shows one embodiment of the present invention wherein the intravascular catheter is positioned as in FIG. 2 and, additionally, the heart is fitted with an external patch electrode.

In certain situations, the unitary catheter system will not function to provide the required cardioverting energy and an additional external patch electrode 120 is required. Typical external patch electrodes are described in commonly assigned U.S. Pat. No. 3,942,536. Patch electrode 120 comprises the patch 122, the patch lead 124, said patch lead 124 terminating in a proximal boot 101' and male plug 104', male plug 104' insertable into the implantable device in place of male plug 104.

In operation, it is contemplated that the anesthetized patient has the catheter system intravascularly inserted into the heart, for example, as in FIG. 2. At this point, fibrillation is induced in order to test the functioning of the system and to provide information regarding threshold energy requirement levels. If the single catheter system is insufficient, the patient is fitted with a patch electrode 120. At the same time, male plug 104 is disengaged from the implantable device and sealed to prevent penetration by body fluids. Male plug 104' is inserted into the implantable device to provide bipolar defibrillation through patch electrode 120 and proximal electrode 48, inserted into the implantable unit through male plug 108. By disengaging and sealing male plug 104, only the defibrillating characteristic of intermediate electrode 18 is affected. The pacing and sensing function of intermediate electrode 18 remains intact, connection to the implantable device occurring through male plugs 94 and 96.

Having now fully described the invention it will be apparent to one of ordinary skill in the art that many changes and modifications can be made thereto without departing from the spirit and scope of the invention as set forth herein.

What is claimed is:

1. An intravacular catheter electrode assembly adapted to operate in a pacing, a cardioverting and a plurality of sensing modes comprising:
   an elongated electrically insulated catheter body having a distal end;
   a first electrode positioned on said distal end of said catheter body;
   a second electrode positioned on said catheter body proximally of said first electrode and spaced a predetermined distance from said first electrode;
   a third electrode positioned on said catheter body between and spaced from said first and second electrodes;
   first connecting means having a first pair of input/output connectors for configuring said first and third electrodes as a pacing electrode pair during said pacing mode and a first sensing electrode pair during one of said plurality of sensing modes; and
   second connecting means having a second pair of input/output connectors for configuring said second and third electrodes as a second sensing electrode pair during a second of said plurality of sensing mode and a cardioverting electrode pair during said cardioverting mode.

2. The catheter assembly of claim 1, wherein the distance between said first and third electrodes is substantially less than the distance between said second and third electrodes.

3. The catheter assembly of claim 1, wherein said catheter body, said second electrode and said third electrode are flexible.

4. The catheter assembly of claim 1, wherein said first and third electrodes are spaced apart such that the heart rate is sensed during said one of said plurality of sensing modes which utilizes said first sensing electrode pair.

5. The catheter assembly of claim 1, wherein said second and third electrodes are spaced apart such that the probability density function is sensed during said second of said plurality of sensing modes which utilizes said second electrode sensing pair.

6. The catheter of claim 1, wherein said first electrode is spaced apart from said third electrode by a distance of about 4 mm and said third electrode is spaced apart from said second electrode by a distance of about 11 centimeters.

7. The catheter of claim 1, wherein said third electrode comprises a low impedance electrically conductive wound wire surface and said second electrode comprises a low impedance electrically conductive wound wire surface.

8. The catheter of claim 7, further comprising sealing means for providing electrical insulation between said first electrode and said third electrode, and between said third electrode and said second electrode.

9. The catheter of claim 8 wherein said sealing means also seals the internal catheter portions of said catheter from body fluids.

10. An intravascular multiple electrode unitary catheter adapted to deliver pacing and cardioverting signals to the heart and adapted to carry a plurality of sensing signals from the heart comprising a flexible elongated body having a distal end and a proximal region, a distal electrode thereon for sensing and pacing, an intermediate electrode thereon for sensing, pacing and cardioverting, and a proximal electrode thereon for cardioverting and sensing, said intermediate and proximal electrodes each comprising an electrically conductive close wound wire surface approximating the low impedance of a continuous metal surface and still maintaining sufficient mechanical flexibility to provide ease of insertion, the catheter further comprising two pair of input/output connectors, a first pair thereof coupled to said distal and said intermediate electrodes and adapted to deliver said pacing signals and carry one of said plurality of sensing signals from said heart, a second pair of said two pair of input/output connectors coupled to said intermediate and said proximal electrodes and adapted to deliver said cardioverting signals and carry a second one of said plurality of sensing signals from the heart.

* * * * *